United States Patent
Isozaki et al.

(10) Patent No.: US 12,070,771 B2
(45) Date of Patent: Aug. 27, 2024

(54) VIBRATION SIGNAL GENERATION DEVICE

(71) Applicant: PIONEER CORPORATION, Tokyo (JP)

(72) Inventors: Kenta Isozaki, Kawagoe (JP); Takashi Morishige, Kawagoe (JP)

(73) Assignee: PIONEER CORPORATION, Tokyo (JP)

( * ) Notice: Subject to any disclaimer, the term of this patent is extended or adjusted under 35 U.S.C. 154(b) by 14 days.

(21) Appl. No.: 17/922,329

(22) PCT Filed: Apr. 30, 2020

(86) PCT No.: PCT/JP2020/018290
§ 371 (c)(1),
(2) Date: Oct. 28, 2022

(87) PCT Pub. No.: WO2021/220471
PCT Pub. Date: Nov. 4, 2021

(65) Prior Publication Data
US 2023/0166292 A1    Jun. 1, 2023

(51) Int. Cl.
*B06B 1/02*     (2006.01)
*A61M 21/00*   (2006.01)
*G10L 21/16*    (2013.01)

(52) U.S. Cl.
CPC ............... *B06B 1/02* (2013.01); *G10L 21/16* (2013.01); *A61M 2021/0005* (2013.01)

(58) Field of Classification Search
CPC .. B06B 1/02; G10L 21/16; A61M 2021/0005; A61M 2021/0022; A61M 2230/06; A61M 2230/60; A61M 21/02
See application file for complete search history.

(56) References Cited

U.S. PATENT DOCUMENTS

| | | | |
|---|---|---|---|
| 11,238,718 B2 * | 2/2022 | Yasushi | A61M 21/00 |
| 11,288,965 B2 * | 3/2022 | Fukuda | G08B 21/00 |
| 2020/0184822 A1 * | 6/2020 | Fukuda | B60W 50/16 |
| 2021/0241596 A1 * | 8/2021 | Yasushi | B06B 1/0284 |

(Continued)

FOREIGN PATENT DOCUMENTS

| | | | | |
|---|---|---|---|---|
| EP | 3677470 A1 * | 7/2020 | | B60K 35/00 |
| EP | 3789124 A1 * | 3/2021 | | A61M 21/00 |

(Continued)

OTHER PUBLICATIONS

International Search Report for PCT/JP2020/018290 dated Aug. 11, 2020, 6 pages.

(Continued)

*Primary Examiner* — Daniel Pihulic

(74) *Attorney, Agent, or Firm* — NIXON & VANDERHYE

(57) ABSTRACT

A desired effect can be exerted on the mental and physical state of a listener of a piece of music with a vibration based on the piece of music even when the piece of music has almost no relaxation or awakening effect. As a vibration signal for vibrating a vibration generation device while the piece of music is being played, the audio signal in the band corresponding to the mode is extracted from the audio signal of the music, and a vibration signal is generated based on the extracted audio signal.

19 Claims, 5 Drawing Sheets

(56) References Cited

U.S. PATENT DOCUMENTS

| | | | | |
|---|---|---|---|---|
| 2021/0379328 A1 | * | 12/2021 | Isozaki | A61M 21/00 |
| 2023/0166292 A1 | * | 6/2023 | Isozaki | B06B 1/02 |
| | | | | 367/140 |
| 2024/0105158 A1 | * | 3/2024 | Isozaki | B06B 1/0223 |

FOREIGN PATENT DOCUMENTS

| | | | | | |
|---|---|---|---|---|---|
| EP | 3677470 | A4 | * | 5/2021 | B60K 35/00 |
| EP | 3863300 | A1 | * | 8/2021 | A61M 21/00 |
| EP | 3789124 | A4 | * | 1/2022 | A61M 21/00 |
| EP | 3863300 | A4 | * | 6/2022 | A61M 21/00 |
| EP | 4145847 | A1 | * | 3/2023 | A61M 21/02 |
| JP | 59-174090 | | | 10/1984 | |
| JP | 61-259669 | | | 11/1986 | |
| JP | 2001-86580 | | | 3/2001 | |
| JP | 2004-274731 | | | 9/2004 | |
| JP | 2004-275668 | | | 10/2004 | |
| JP | 2019043327 | A | * | 3/2019 | |
| JP | 2019046081 | A | * | 3/2019 | |
| JP | 2019147124 | A | * | 9/2019 | |
| JP | 2019151189 | A | * | 9/2019 | |
| JP | 2019152503 | A | * | 9/2019 | |
| JP | 2019193699 | A | * | 11/2019 | |
| JP | 2020-57954 | | | 4/2020 | |
| JP | 2020056932 | A | * | 4/2020 | |
| JP | 2020056933 | A | * | 4/2020 | |
| JP | 2020057954 | A | * | 4/2020 | |
| JP | 2020057955 | A | * | 4/2020 | |
| JP | 2021175146 | A | * | 11/2021 | |
| WO | WO-2011155028 | A1 | * | 12/2011 | A61H 23/0236 |
| WO | WO-2019044826 | A1 | * | 3/2019 | B60K 35/00 |
| WO | WO-2019211990 | A1 | * | 11/2019 | A61M 21/00 |
| WO | WO-2020071136 | A1 | * | 4/2020 | A61M 21/00 |
| WO | WO-2020209140 | A1 | * | 10/2020 | |
| WO | WO-2021220471 | A1 | * | 11/2021 | A61M 21/02 |

OTHER PUBLICATIONS

Written Opinion of the ISA for PCT/JP2020/018290 dated Aug. 11, 2020, 4 pages.

* cited by examiner

VIBRATION SIGNAL GENERATION DEVICE

CROSS-REFERENCE TO RELATED APPLICATIONS

This application is the U.S. national phase of International Application No. PCT/JP2020/018290 filed Apr. 30, 2020 which designated the U.S., the entire contents of which are hereby incorporated by reference.

BACKGROUND OF THE INVENTION

Field of the Invention

The present invention relates to a vibration signal generation device.

Description of the Related Art

Techniques have been developed that, while a piece of music is being played, applies vibration based on the piece of music to a listener of the piece of music. For example, Patent Literature 1 discloses a technique in which an audio signal of a piece of music played on a car audio system of a four-wheel private vehicle is processed and converted into a low frequency sound signal. The low frequency sound signal is then transmitted to a transducer inside a seat cushion, and the transducer causes the low frequency sound to oscillate. Patent Literature 1 also discloses using a relaxing piece of music or a relaxing vibration pattern to obtain a relaxation effect, or using a piece of music or vibration pattern effective for awakening the user to obtain an awakening effect.

CITATION LIST

Patent Literature

Patent Literature 1: JP 2004-275668 A

However, Patent Literature 1 does not disclose a method of obtaining a relaxation effect or an awakening effect by using a piece of music that is not effective for either relaxation or awakening.

SUMMARY OF THE INVENTION

An example of the problems to be solved by the present invention is to make it possible to achieve a desired effect on the mental and physical state of the listener of the piece of music with a vibration based on the piece of music even when it has almost no relaxation or awakening effect.

In order to solve the above problem, a first embodiment of the invention is a vibration signal generation device that generates a vibration signal for vibrating a vibration generation device while a piece of music is being played, the vibration signal generation device including: a mode determination unit that determines a mode from a plurality of modes; an extraction unit that extracts, from the audio signal of the piece of music, the audio signal in the band corresponding to the mode determined by the mode determination unit; and a generation unit that generates the vibration signal based on the audio signal extracted by the extraction unit.

Another embodiment is a vibration signal generation method executed by a computer to generate a vibration signal for vibrating a vibration generation device while a piece of music is being played, the vibration signal generation method including: a mode determination step of determining a mode from a plurality of modes; an extraction step of extracting, from the audio signal of the piece of music, the audio signal in the band corresponding to the mode determined by the mode determination unit; and a generation step of generating the vibration signal based on the audio signal extracted by the extraction unit.

A further embodiment is a vibration signal generation program that causes a computer to execute the vibration signal generation method.

Yet a further embodiment includes storing the vibration signal generation program.

DESCRIPTION OF THE PREFERRED EMBODIMENTS

Figure 1:
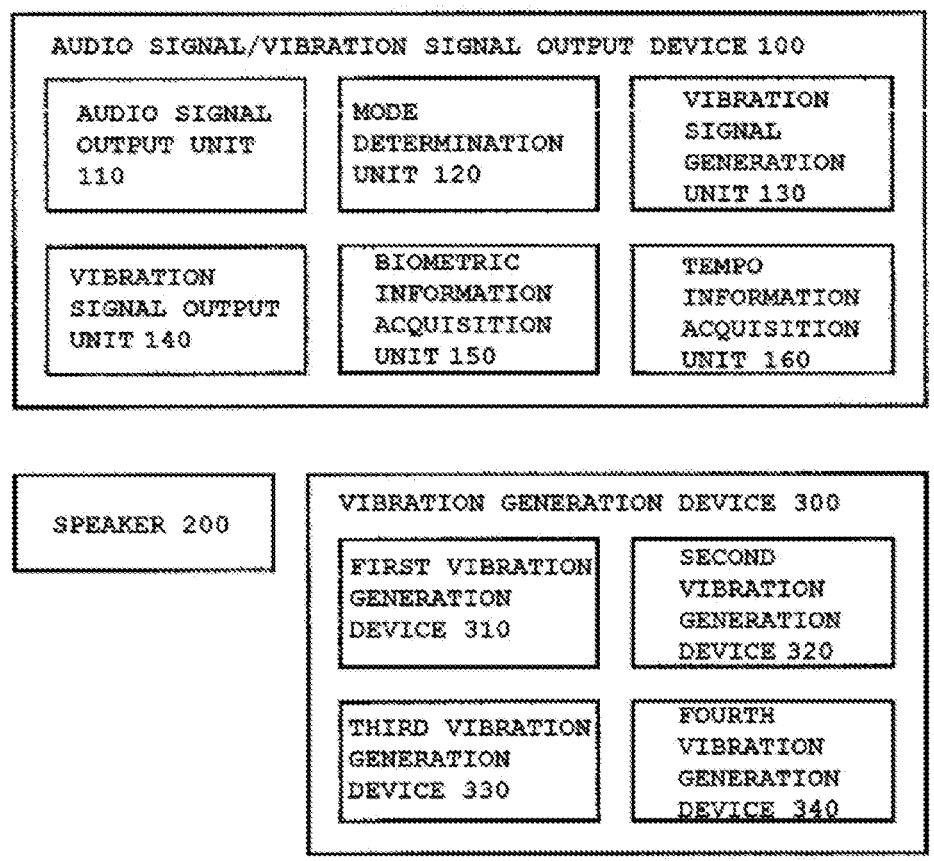
FIG. 1 is a diagram illustrating an audio signal/vibration signal output device 100 according to an example of the present invention.

A vibration signal generation device according to an embodiment of the present invention generates a vibration signal for vibrating a vibration generation device while a piece of music is being played, the vibration signal generation device including: a mode determination unit that determines a mode from a plurality of modes; an extraction unit that extracts, from the audio signal of the piece of music, the audio signal in the band corresponding to the mode determined by the mode determination unit; and a generation unit that generates the vibration signal based on the audio signal extracted by the extraction unit. Therefore, in the present embodiment, vibration in a band corresponding to the desired effect can be applied to the listener of the piece of music. As a result, in this embodiment, it is possible to achieve a desired effect on the mental and physical state of the listener of the piece of music with a vibration based on the piece of music even when the piece of music has almost no relaxation or awakening effect.

The plurality of modes may include a first mode for a relaxation effect, the extraction unit may extract, when the determined mode is the first mode, an audio signal in a first band from the audio signal of the piece of music, and at least part of the first band may have a frequency below a band for another mode. The plurality of modes may further include a second mode for an awakening effect, the extraction unit may extract, when the determined mode is the second mode, an audio signal in a second band from the audio signal of the piece of music, and at least part of the second band may have a frequency above a band for another mode. At least part of the second band may have a frequency above the first band. This makes it possible to apply to the user a vibration in a band corresponding to the desired effect. As a result, in this embodiment, it is possible to achieve a desired effect on the mental and physical state of the listener of the piece of music with a vibration based on the piece of music even when the piece of music has almost no relaxation or awakening effect.

The vibration generation device may be embedded in a seat on which a user can sit. This makes it possible to exert the desired effect on the mental and physical state of the user when the user is seated.

The vibration generation device may include a first vibration generation device embedded in a part facing the back of the user seated on the seat, and a second vibration generation device embedded in a part facing the waist of the user seated on the seat, the vibration signal may include a first vibration signal for vibrating the first vibration generation device and a second vibration signal for vibrating the second vibration generation device, and the first band for the second vibration signal may be narrower than the first band for the first vibration signal. This makes it possible to generate a suitable vibration for each body part, and exert a relaxation effect on the user more effectively.

The vibration signal generation unit may generate the first and second vibration signals so that, when the determined mode is the first mode, the intensity of vibration generated by the first vibration generation device is higher than the intensity of vibration generated by the second vibration generation device. The vibration signal generation unit may generate the first and second vibration signals so that, when the determined mode is the second mode, the intensity of vibration generated by the second vibration generation device is higher than the intensity of vibration generated by the first vibration generation device. As a result, the relaxation effect and the awakening effect can be more effectively exerted on the user.

The vibration signal generation device may further include a biometric signal acquisition unit that acquires biometric information of a user seated on the seat, and the mode determination unit may determine the mode based on the acquired biometric information. This makes it possible to exert an effect on the user according to the user's mental and physical state.

A vibration signal generation method according to an embodiment of the present invention is executed by a computer to generate a vibration signal for vibrating a vibration generation device while a piece of music is being played, the vibration signal generation method including: a mode determination step of determining a mode from a plurality of modes; an extraction step of extracting, from the audio signal of the piece of music, the audio signal in the band corresponding to the mode determined by the mode determination unit; and a generation step of generating the vibration signal based on the audio signal extracted by the extraction unit. Therefore, in the present embodiment, vibration in a band corresponding to the desired effect can be applied to the listener of the piece of music. As a result, in this embodiment, it is possible to achieve a desired effect on the mental and physical state of the listener of the piece of music with a vibration based on the piece of music even when the piece of music has almost no relaxation or awakening effect.

A vibration signal generation program according to an embodiment of the present invention causes a computer to execute the above-described vibration signal generation method. Therefore, in this embodiment, it is possible to achieve a desired effect on the mental and physical state of the listener of the piece of music with a computer using a vibration based on the piece of music, even when the piece of music has almost no relaxation or awakening effect.

A computer-readable storage medium according to an embodiment of the present invention stores the above-described vibration signal generation program. Therefore, in the present embodiment, in addition to being distributed as a device incorporating the vibration signal generation program, it can be distributed alone, which facilitates version upgrade and the like.

EXAMPLES

<Audio Signal/Vibration Signal Output Device 100>

FIG. 1 is a diagram illustrating an audio signal/vibration signal output device 100 according to an example of the present invention. The audio/vibration signal output device 100 according to the present example outputs, in addition to an audio signal of a piece of music to a speaker 200, a vibration signal generated based on the audio signal of the piece of music to a vibration generation device 300 so as to also apply vibration to a listener (user) of the piece music and achieve a desired effect on the mental and physical state of the user.

The audio signal/vibration signal output device 100 according to the present example includes an audio signal output unit 110 that outputs an audio signal of a piece of music, a mode determination unit 120 that determines one mode from a plurality of modes related to changes in the mental and physical state, a vibration signal generation unit 130 that generates a vibration signal from the audio signal of the piece of music, and a vibration signal output unit 140 that outputs the vibration signal.

The audio signal output unit 110 acquires the data of the piece of music stored in a storage device, a storage medium such as a compact disc (CD), a cloud, or the like, generates the audio signal of the piece of music from the acquired data, and outputs the generated audio signal to the vibration signal generation unit 130 and the speaker 200.

The mode determination unit 120 determines a mode from the plurality of modes related to changes in the mental and physical state. For example, the mode determination unit 120 preferably determines the mode based on a user's input. For example, the audio signal/vibration signal output device 100 preferably includes a unit that receives an input from the user. The audio signal/vibration signal output device 100 may also include a means for acquiring a feature of the piece of music, and the mode determination unit 120 may determine the mode based on this feature of the piece of music. The audio signal/vibration signal output device 100 may further include a means for learning the effect the user wishes to obtain by playing a certain piece of music by machine learning, and the mode determination unit 120 may determine the mode based on the learning results.

The vibration signal generation unit 130 acquires the audio signal output from the audio signal output unit 110 and generates a vibration signal from the audio signal. The vibration signal generation unit 130 extracts, for example, a low-range (for example, 20 Hz to 100 Hz) part of the audio signal, and generates a vibration signal based on the extracted part. The vibration signal is a signal having the low-range frequency components of the audio signal. The vibration signal generation unit 130 preferably includes, for example, a band-pass filter or a low-pass filter that extracts part of the audio signal. Further, as will be described in detail below, the vibration signal generation unit 130 may generate a vibration signal from the audio signal according to the mode determined by the mode determination unit 120.

The vibration signal output unit 140 outputs the vibration signal generated by the vibration signal generation unit 130 to the vibration generation device 300. The vibration generation device 300 is a device that generates vibration based on an input vibration signal, and is, for example, embedded in a seat on which a user can sit. The vibration signal output unit 130 may output the vibration signal so that it is synchronized with the audio signal output from the audio signal output unit 110, or as described in detail below, may output the vibration signal at a time shifted from the time it is synchronized with the audio signal output from the audio signal output unit 110 by a time corresponding to the mode determined by the mode determination unit 120.

As described above, the audio signal/vibration signal output device 100 according to the present example not only outputs the sound of a piece of music from the speaker 200 but also enables the vibration generation device 300 to generate vibration based on the audio signal of the piece of music. As a result, in this example, it is possible to apply vibration based on the piece of music to the listener (user) thereof.

Figure 2:
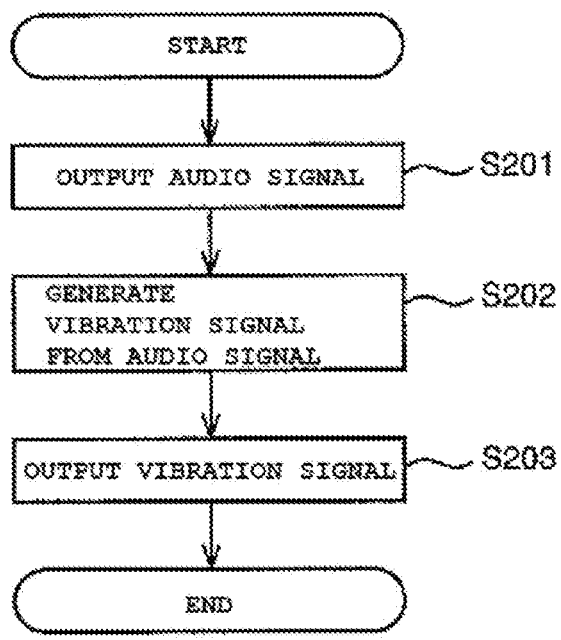
FIG. 2 is a diagram illustrating an example of a processing operation of an audio signal/vibration signal output device 100 according to an example of the present invention.

FIG. 2 is a diagram illustrating an example of a processing operation of the audio signal/vibration signal output device 100 according to the present example. The audio signal output unit 110 outputs the audio signal of the piece of music to the vibration signal generation unit 130 and the speaker 200 (step S201). The vibration signal generation unit 130 generates a vibration signal from the audio signal (step S202), and the vibration signal output unit 140 outputs the vibration signal generated by the vibration signal generation unit 130 to the vibration generation device 300 (step S203).

Frequency Band of Vibration Signal and Changes in Mental and Physical State

Figure 3:
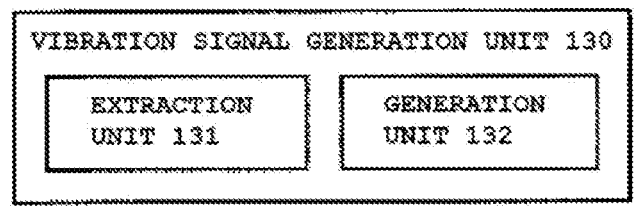
FIG. 3 is a diagram illustrating a vibration signal generation unit 130 according to an example of the present invention.

FIG. 3 is a diagram illustrating the vibration signal generation unit 130 according to an example of the present invention. The vibration signal generation unit 130 according to the present example includes an extraction unit 131 and a generation unit 132. The extraction unit 131 extracts the audio signal in the band corresponding to the mode determined by the mode determination unit 120, and the generation unit 132 generates the vibration signal based on the audio signal extracted by the extraction unit 131.

The inventors have found that, when a user is listening to a piece of music having a relaxation effect, and vibrations of the lower frequency band of the low range of this piece of music are applied to the user, the parasympathetic nervous system of the user is further activated, which means that the user becomes more relaxed. The inventors have also found that, when a user is listening to a piece of music having an awakening effect, and vibrations of the higher frequency band of the low range of this piece of music are applied to the user, the sympathetic nervous system of the user is further activated, which means that the user becomes more awake.

Further, the inventors have found that, even when the piece of music has almost no relaxation effect or awakening effect (an intermediate piece of music), when the user is listening to this piece of music, and vibrations of the lower frequency band of the low range of the piece of music are applied to the user, the parasympathetic nervous system of the user is activated, which means that the user becomes relaxed. The inventors have also found that, when a user is listening to an intermediate piece of music, and vibrations of the higher frequency band of the low range of this piece of music are applied to the user, the sympathetic nervous system of the user is activated, which means that the user becomes awake.

In view of the above, in the present example, the plurality of modes include a healing mode (first mode) for relaxing the user and an awakening mode (second mode) for awakening the user.

When the mode determined by the mode determination unit 120 is the healing mode, the extraction unit 131 extracts the audio signal in a first band from the audio signal of the piece of music, and when the mode determined by the mode determination unit 120 is the awakening mode, the extraction unit extracts the audio signal in a second band from the audio signal of the piece of music. At least part of the first band has frequencies below the band for another mode, and at least part of the second band has frequencies above the band for another mode. In particular, the first band is a band including frequencies lower than those in the second band. The first and the second bands may either partially overlap or not.

The plurality of modes may include modes other than the healing mode and awakening mode. For example, the plurality of modes may include a third mode for achieving an effect other than relaxation and awakening. For example, when the mode determined by the mode determination unit 120 is the third mode, the extraction unit 131 preferably extracts the audio signal of a third band including frequencies above the first band and frequencies below the second band from the audio signal of the piece of music.

The audio signal/vibration signal output device 100 may further include a biometric information acquisition unit 150 that acquires biometric information of the user. Then, the mode determination unit 120 may determine the mode based on the biometric information acquired by the biometric information acquisition unit 150.

For example, the biometric information acquisition unit 150 preferably acquires information related to the heartbeat of the user as the biometric information of the user. Information related to the heartbeat of the user includes information related to the heart rate of the user and the heart rate variability of the user (for example, the low frequency (LF) and high frequency (RF) of the heart rate variability, and the ratio LF/HF between LF and HF). It is possible to learn the mental and physical state from the information related to the heart rate and heart rate variability. For example, when the user is relaxed, the heart rate is low, and when the user is awake, the heart rate is high. Therefore, for example, preferably, when the biometric information acquired by the biometric information acquisition unit 150 indicates that the user is relaxed, the mode determination unit 120 determines to use the awakening mode to awaken the user, and when the biometric information acquired by the biometric information acquisition unit 150 indicates that the user is awake, it determines to use the healing mode to relax the user. This makes it possible to exert an effect on the user according to the user's mental and physical state.

Figure 4:
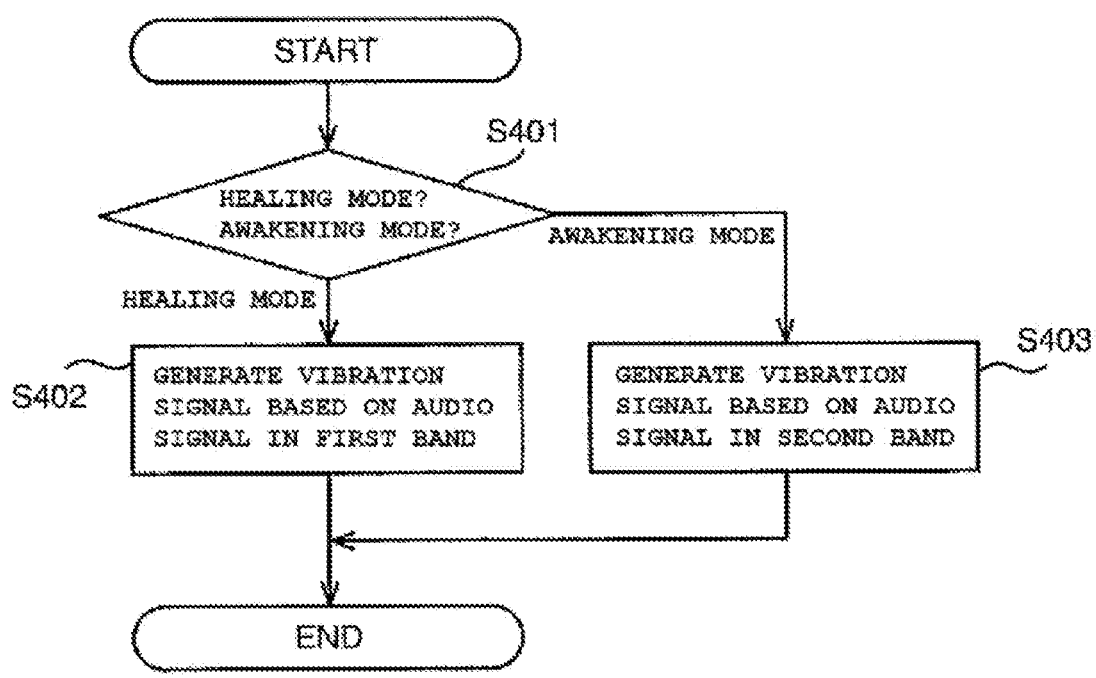
FIG. 4 is a diagram illustrating an example of a processing operation of a vibration signal generation unit 130 according to an example of the present invention.

FIG. 4 is a diagram illustrating an example of a processing operation of the vibration signal generation unit 130 according to the present example. The processing operation illustrated in FIG. 4 is executed in, for example, step S202 of the processing operation illustrated in FIG. 2. The processing operation illustrated in FIG. 4 is a processing operation carried out when the plurality of modes includes only the healing mode and awakening mode.

When the mode determined by the mode determination unit 120 is the healing mode (step S401, healing mode), the extraction unit 131 extracts the audio signal in the first band, and the generation unit 132 generates the vibration signal based on the extracted audio signal in the first band (step S402). When the mode determined by the mode determination unit 120 is the awakening mode (step S401, awakening mode), the extraction unit 131 extracts the audio signal in the second band, and the generation unit 132 generates the vibration signal based on the extracted audio signal in the second band (step S403).

Generation of Vibration Signal for Each Body Part to which Vibration is Applied

Figure 5:
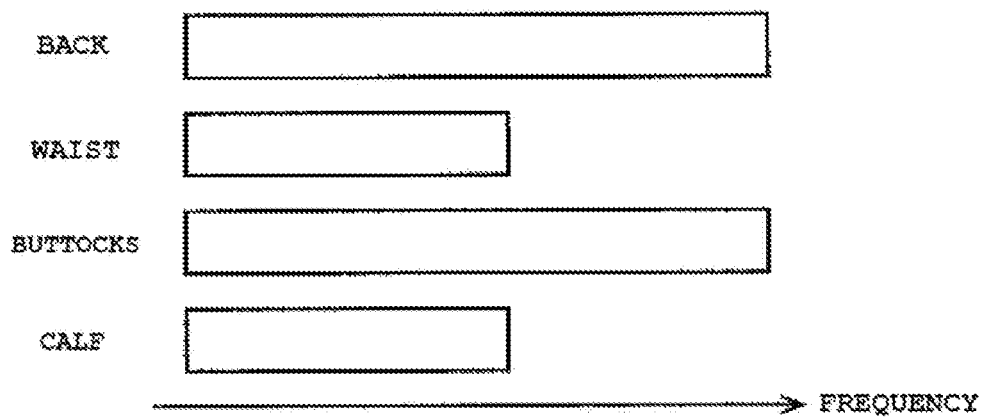
FIG. 5 is a diagram illustrating examples of frequency bands in which a vibration can have a relaxation effect.

The inventors have found that the vibration that can provide the desired effect varies depending on the body part. In particular, the width of the frequency band of vibration that can provide a relaxation effect to the user is different between a case where vibration is applied to the back or buttocks and a case where vibration is applied to the waist or calf. FIG. 5 is a diagram illustrating examples of frequency bands in which the vibration can have a relaxation effect. As illustrated in FIG. 5, the frequency band of the vibration that can provide the relaxation effect is narrower for the waist and calf than for the back and buttocks.

Therefore, in an example of the present invention, in order to apply vibrations to a plurality of body parts of the user, the vibration generation device 300 includes a plurality of vibration generation devices embedded in, for example, a plurality of parts of the seat on which the user can sit. In this example, the vibration signal generated by the vibration signal generation unit 130 includes a plurality of vibration signals in order to vibrate the plurality of vibration generation devices independently.

For example, the vibration generation device 300 includes a first vibration generation device 310 that applies vibration to the back of the user, a second vibration generation device 320 that applies vibration to the waist of the user, a third vibration generation device 330 that applies vibration to the buttocks of the user, and a fourth vibration generation device 340 that applies vibration to the calf of the user. For example, the first vibration generation device 310 is embedded in a part facing the back of the user seated on the seat, the second vibration generation device 320 is embedded in a part facing the waist of the user seated on the seat, the third vibration generation device 330 is embedded in a part facing the buttocks of the user seated on the seat, and the fourth vibration generation device 340 is embedded in a part facing the calf of the user seated on the seat.

In addition, for example, the vibration signals generated by the vibration signal generation unit 130 include a first vibration signal for vibrating the first vibration generation device 310, a second vibration signal for vibrating the second vibration generation device 320, a third vibration signal for vibrating the third vibration generation device 330, and a fourth vibration signal for vibrating the fourth vibration generation device 340.

For example, the widths of the frequency distributions of the second and fourth vibration signals are preferably smaller than the widths of the frequency distributions of the first and third vibration signals. That is, the first bands for the second and fourth vibration signals are preferably narrower than the first bands for the first and third vibration signals.

This makes it possible to generate a suitable vibration for each body part, and exert a relaxation effect on the user more effectively.

Vibration Signal Output Timing and Changes in Mental and Physical State

Figure 6:
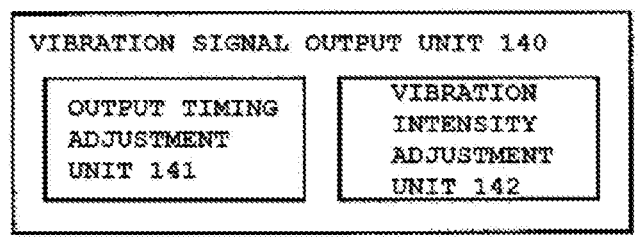
FIG. 6 is a diagram illustrating a vibration signal output unit 140 according to an example of the present invention.

FIG. 6 is a diagram illustrating the vibration signal output unit 140 according to an example of the present invention. As described above, the vibration signal is a signal obtained by extracting a partial band of the audio signal of a piece of music. Therefore, after extracting the signal, if neither the audio signal nor the vibration signal is delayed, the audio signal and the vibration signal are output synchronously. However, the inventors have found that, when a user is listening to a piece of music having a relaxation effect, and vibrations based on this piece of music are not synchronized with the piece of music and applied to the user with a delay from the piece of music, the parasympathetic nervous system of the user is further activated, which means that the user becomes more relaxed. In addition, the inventors have found that, when a user is listening to a piece of music having an awakening effect, and vibrations based on this piece of music are not synchronized with the piece of music and applied to the user ahead of the piece of music, the sympathetic nervous system of the user is further activated, which means that the user becomes more awake.

The inventors also have found that, when a user is listening to an intermediate piece of music, and vibration based on this piece of music is not synchronized with the piece of music and applied to the user with a delay from the piece of music, the parasympathetic nervous system of the user is activated, which means that the user becomes relaxed. The inventors also have found that, when a user is listening to an intermediate piece of music, and vibration based on this piece of music is not synchronized with the piece of music and applied to the user ahead of the piece of music, the sympathetic nervous system of the user is activated, which means that the user becomes awake.

In view of the above, the vibration signal output unit 140 according to the present example includes an output timing adjustment unit 141. The output timing adjustment unit 141 shifts the vibration signal from the time it is synchronized with the piece of music by a certain time according to the mode determined by the mode determination unit 120. As a result, the audio signal/vibration signal output device 100 according to the present example outputs the audio and vibration signals to the vibration generation device 300 with a certain shift in time between them.

For example, when the mode determined by the mode determination unit 120 is the healing mode, the audio signal/vibration signal output device 100 outputs the vibration signal delayed by a first time from the time it is synchronized with the audio signal of the piece of music, and when the mode determined by the mode determination unit 120 is the awakening mode, the audio signal/vibration signal output device outputs the vibration signal earlier than the time it is synchronized with the audio signal of the piece of music by a second time.

At this time, for example, preferably, when the mode determined by the mode determination unit 120 is the healing mode, the output timing adjustment unit 141 delays the vibration signal from the audio signal of the piece of music by the first time, and when the mode determined by the mode determination unit 120 is the awakening mode, the output timing adjustment unit delays the audio signal from the vibration signal of the piece of music by the second time.

When the values of the first time and the second time are large relative to the tempo of the piece of music, that is, the beat duration of the piece of music, the user may feel uncomfortable due to the excessive shift between the audio signal and vibration signal. In view of this, the audio signal/vibration signal output device 100 according to an example of the present invention further includes a tempo information acquisition unit 160 that acquires information on the tempo of the piece of music such as the beat duration of the piece music and the number of beats per unit time (for example, BPM (Beat Per Minute)). In the present example, the first time and the second time are determined to be smaller than a threshold based on the information on the tempo.

In general, fast-tempo music has an awakening effect, and a user listens to fast-tempo music when he or she wants the awakening effect. However, when the value of the second time, which is the shift between the audio signal and vibration signal, is increased to a value that is smaller than the beat duration by about one order of magnitude, the user feels uncomfortable with the vibration. Therefore, the threshold is preferably, for example, a value that is smaller than the beat duration by one order of magnitude. The threshold preferably decreases as the tempo of the music increases.

Figure 7:
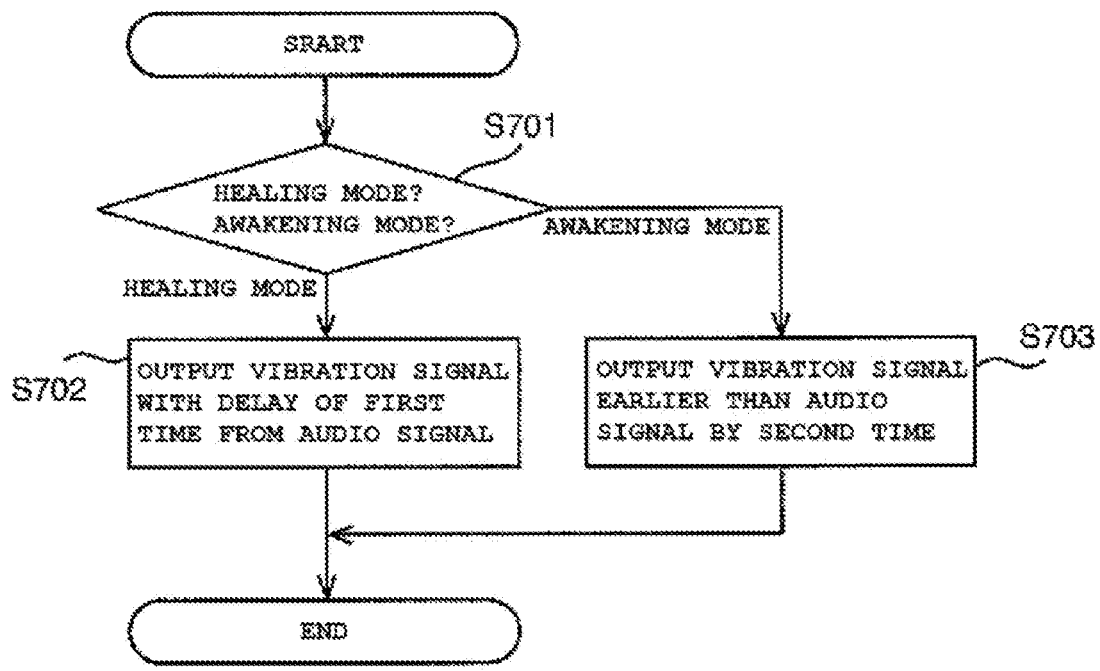
FIG. 7 is a diagram illustrating an example of a processing operation of a vibration signal output unit 140 according to an example of the present invention.

FIG. 7 is a diagram illustrating an example of a processing operation of the vibration signal output unit 140 according to the present example. The processing operation illustrated in FIG. 7 is executed in, for example, step S203 of the processing operation illustrated in FIG. 2. The processing operation illustrated in FIG. 7 is a processing operation carried out when the plurality of modes includes only the healing mode and awakening mode.

When the mode determined by the mode determination unit 120 is the healing mode (step S701, healing mode), the audio signal/vibration signal output device 100 outputs the vibration signal with a delay of the first time from the time it is synchronized with the audio signal of the piece of music (step S702). When the mode determined by the mode determination unit 120 is the awakening mode (step S701, awakening mode), the audio signal/vibration signal output device 100 outputs the vibration signal earlier than the time it is synchronized with the audio signal of the piece of music by the second time (step S703).

Output Timing of Vibration for Each Body Part to which Vibration is Applied

Figure 8:
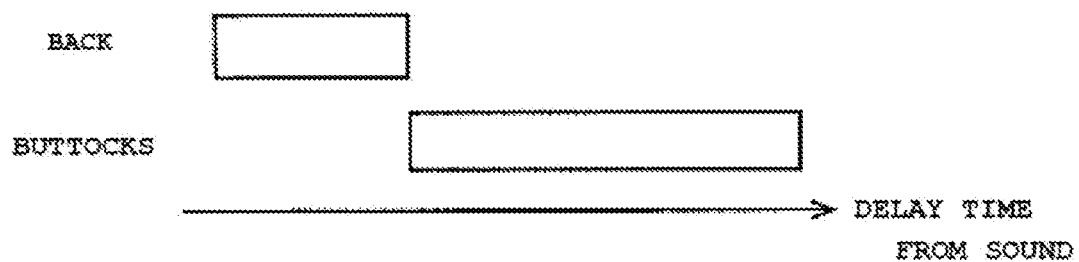
FIG. 8 is a diagram illustrating examples of the delay time from the sound with which the vibration can have a relaxation effect.

The inventors have found that the vibration that can provide the desired effect varies depending on the body part. In particular, the delay time (that is, the first time) from the sound with which the vibration can have a relaxation effect on the user is different between when the vibration is applied to the back and when the vibration to the buttocks. FIG. 8 is a diagram illustrating examples of the delay time from the sound with which the vibration can have a relaxation effect. As illustrated in FIG. 8, the delay time from the sound with which the vibration can have a relaxation effect is shorter for the back than for the buttocks.

Therefore, in the audio signal/vibration signal output device 100 according to an example of the present invention, the first vibration signal (vibration signal for vibrating the first vibration signal that applies vibration to the back of the user) has a larger delay than the third vibration signal (the vibration signal for vibrating the third vibration signal that applies vibration to the buttocks of the user). That is, in the present example, the first time, which is the shift between the audio signal and vibration signal, is shorter for the first vibration signal than for the third vibration signal. This makes it possible to generate a suitable vibration for each body part, and exert a relaxation effect on the user more effectively.

Similarly, the second time may also be changed depending on the vibration signal. For example, the first time and the second time, which are the shifts between the audio signal and vibration signal, may be set in advance for each vibration signal.

As described above, when the tempo of the music increases, the beat duration becomes close to the shift (the first time and second time) between the audio signal and vibration signal, which makes the user feel uncomfortable with the vibration. Therefore, the first time and the second time are preferably determined to be smaller than the threshold based on information on the tempo.

Figure 9:
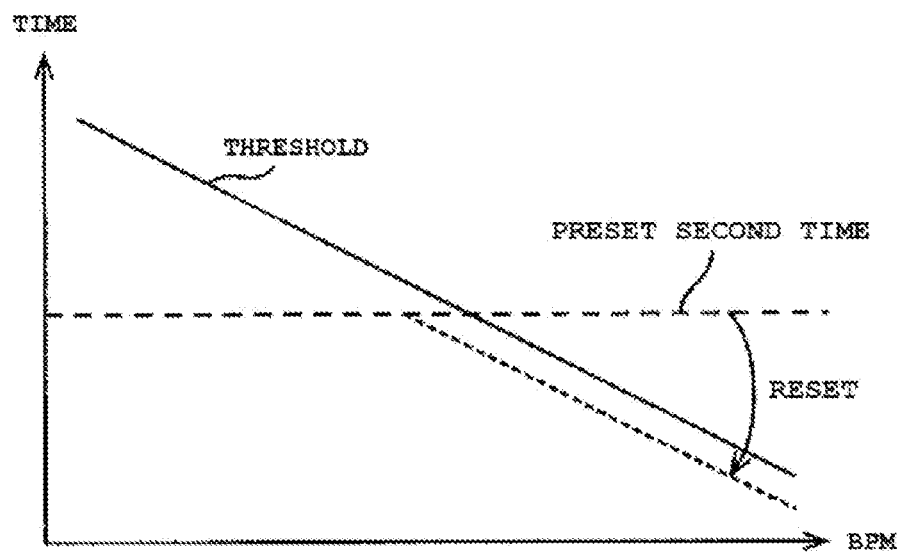
FIG. 9 is a diagram for explaining the resetting of the predetermined second time.

However, as illustrated in FIG. 9, when the threshold decreases as the tempo of the music increases (as the BPM increases in FIG. 9), and each vibration signal has a preset second time, the second time may exceed the threshold when the tempo of the music becomes higher than or equal to a certain rate. In such a case, the value of the second time is preferably reset to be smaller than the threshold.

Vibration Intensity for Each Body Part to which Vibration is Applied

The inventors have found that the effect of a vibration varies depending on the body part. In particular, a vibration to the back contributes more to the relaxation effect, and a vibration to the waist contributes more to the awakening effect.

In view of this, the vibration signal output unit 140 according to an example of the present invention includes a vibration intensity adjustment unit 142. When the mode determined by the mode determination unit 120 is the healing mode, the vibration intensity adjustment unit 142 adjusts the first vibration signal (vibration signal for vibrating the first vibration generation device) and the second vibration signal (vibration signal for vibrating the second vibration generation device) so that the intensity of the vibration generated by the first vibration generation device (vibration generation device that applies vibration to the back of the user) is higher than the intensity of the vibration generated by the second vibration generation device (vibration generation device that applies vibration to the waist of the user). When the mode determined by the mode determination unit 120 is the awakening mode, the vibration intensity adjustment unit 142 adjusts the first and second vibration signals so that the intensity of the vibration generated by the second vibration generation device is higher than the intensity of the vibration generated by the first vibration generation device. Therefore, in the present example, even when the first and second vibration signals are vibration signals based on the same piece of music, the vibration applied to the back is larger than the vibration applied to the waist in the healing mode, and the vibration applied to the waist is larger than the vibration applied to the back in the awakening mode. As a result, in the present example, the relaxation effect and the awakening effect can be more effectively exerted on the user.

The present invention has been described above with reference to preferred embodiments of the present invention. Although the present invention has been described with reference to specific examples, various modifications and changes can be made to these specific examples without departing from the spirit and scope of the present invention specified in the claims.

REFERENCE SIGNS LIST

- 100 Audio signal/vibration signal output device
- 110 Audio signal output unit
- 120 Mode determination unit
- 130 Vibration signal output unit
- 131 Extraction unit
- 132 Generation unit
- 140 Vibration signal output unit
- 141 Output timing adjustment unit
- 142 Vibration intensity adjustment unit
- 150 Biometric information acquisition unit
- 160 Tempo information acquisition unit
- 200 Speaker
- 300 Vibration generation device
- 310 First vibration generation device
- 320 Second vibration generation device
- 330 Third vibration generation device
- 340 Fourth vibration generation device

The invention claimed is:

1. A vibration signal generation device that generates a vibration signal for vibrating a vibration generation device while a piece of music is being played, the vibration signal generation device comprising:
   a mode determination unit that determines a mode from a plurality of modes;
   an extraction unit that extracts, from the audio signal of the piece of music, the audio signal in the band corresponding to the mode determined by the mode determination unit; and
   a generation unit that generates the vibration signal based on the audio signal extracted by the extraction unit, wherein
   the plurality of modes include a first mode for a relaxation effect,
   the extraction unit extracts, when the determined mode is the first mode, an audio signal in a first band from the audio signal of the piece of music, and
   at least part of the first band has a frequency below a band for another mode.

2. The vibration signal generation device according to claim 1, wherein
   the vibration generation device is embedded in a seat on which a user can sit,
   the vibration generation device includes a first vibration generation device embedded in a part facing the back of the user seated on the seat, and a second vibration generation device embedded in a part facing the waist of the user seated on the seat,
   the vibration signal includes a first vibration signal for vibrating the first vibration generation device and a second vibration signal for vibrating the second vibration generation device, and
   the first band for the second vibration signal is narrower than the first band for the first vibration signal.

3. The vibration signal generation device according to claim 1, wherein
   the vibration generation device is embedded in a seat on which a user can sit,
   the vibration generation device includes a first vibration generation device embedded in a part facing the back of the user seated on the seat, and a second vibration generation device embedded in a part facing the waist of the user seated on the seat,
   the vibration signal includes a first vibration signal for vibrating the first vibration generation device and a second vibration signal for vibrating the second vibration generation device, and
   when the determined mode is the first mode, the generation unit generates the first and second vibration signals so that the intensity of vibration generated by the first vibration generation device is higher than the intensity of vibration generated by the second vibration generation device.

4. The vibration signal generation device according to claim 1, wherein
   the plurality of modes further include a second mode for an awakening effect,
   when the determined mode is the second mode, the extraction unit extracts an audio signal in a second band from the audio signal of the piece of music, and
   at least part of the second band has a frequency above a band for another mode.

5. The vibration signal generation device according to claim 4, wherein
   the vibration generation device is embedded in a seat on which a user can sit,
   the vibration generation device includes a first vibration generation device embedded in a part facing the back of the user seated on the seat, and a second vibration generation device embedded in a part facing the waist of the user seated on the seat,
   the vibration signal includes a first vibration signal for vibrating the first vibration generation device and a second vibration signal for vibrating the second vibration generation device, and
   when the determined mode is the second mode, the generation unit generates the first and second vibration signals so that the intensity of vibration generated by the second vibration generation device is higher than the intensity of vibration generated by the first vibration generation device.

6. The vibration signal generation device according to claim 1, wherein
   the plurality of modes include a second mode for an awakening effect,
   the extraction unit extracts, when the determined mode is the second mode, an audio signal in a second band from the audio signal of the piece of music, and
   at least part of the second band has a frequency above the first band.

7. The vibration signal generation device according to claim 6, wherein
   the vibration generation device is embedded in a seat on which a user can sit,
   the vibration generation device includes a first vibration generation device embedded in a part facing the back of the user seated on the seat, and a second vibration generation device embedded in a part facing the waist of the user seated on the seat,
   the vibration signal includes a first vibration signal for vibrating the first vibration generation device and a second vibration signal for vibrating the second vibration generation device, and
   the generation unit generates the first and second vibration signals so that, when the determined mode is the first mode, the intensity of vibration generated by the first vibration generation device is higher than the intensity of vibration generated by the second vibration generation device, and when the determined mode is the second mode, the intensity of vibration generated by the second vibration generation device is higher than the intensity of vibration generated by the first vibration generation device.

8. The vibration signal generation device according to claim 1, wherein the vibration generation device is embedded in a seat on which a user can sit.

9. The vibration signal generation device according to claim 1, further comprising a biometric signal acquisition unit that acquires biometric information of a user seated on the seat,
wherein the mode determination unit determines the mode based on the acquired biometric information.

10. A vibration signal generation method executed by a computer to generate a vibration signal for vibrating a vibration generation device while a piece of music is being played, the vibration signal generation method comprising:
a mode determination step of determining a mode from a plurality of modes;
an extraction step of extracting, from the audio signal of the piece of music, the audio signal in the band corresponding to the mode determined by the mode determination step; and
a generation step of generating the vibration signal based on the audio signal extracted by the extraction step, wherein
the plurality of modes include a first mode for a relaxation effect,
in the extraction step, when the determined mode is the first mode, an audio signal in a first band is extracted from the audio signal of the piece of music, and
at least part of the first band has a frequency below a band for another mode.

11. A non-transitory computer-readable medium on which is stored a vibration signal generation program that causes a computer to execute the vibration signal generation method according to claim 10 when the program is executed by the computer.

12. The vibration signal generation device according to claim 4, wherein the vibration generation device is embedded in a seat on which a user can sit.

13. The vibration signal generation device according to claim 6, wherein the vibration generation device is embedded in a seat on which a user can sit.

14. The vibration signal generation device according to claim 2, further comprising a biometric signal acquisition unit that acquires biometric information of a user seated on the seat,
wherein the mode determination unit determines the mode based on the acquired biometric information.

15. The vibration signal generation device according to claim 3, further comprising a biometric signal acquisition unit that acquires biometric information of a user seated on the seat,
wherein the mode determination unit determines the mode based on the acquired biometric information.

16. The vibration signal generation device according to claim 5, further comprising a biometric signal acquisition unit that acquires biometric information of a user seated on the seat,
wherein the mode determination unit determines the mode based on the acquired biometric information.

17. The vibration signal generation device according to claim 8, further comprising a biometric signal acquisition unit that acquires biometric information of a user seated on the seat,
wherein the mode determination unit determines the mode based on the acquired biometric information.

18. The vibration signal generation device according to claim 12, further comprising a biometric signal acquisition unit that acquires biometric information of a user seated on the seat,
wherein the mode determination unit determines the mode based on the acquired biometric information.

19. The vibration signal generation device according to claim 13, further comprising a biometric signal acquisition unit that acquires biometric information of a user seated on the seat,
wherein the mode determination unit determines the mode based on the acquired biometric information.

* * * * *